United States Patent [19]
Korff et al.

[11] Patent Number: 4,590,306
[45] Date of Patent: May 20, 1986

[54] PROCESS FOR THE CONVERSION OF META/PARA-CRESOL MIXTURES

[75] Inventors: Joachim Korff, Bornheim-Merten; Karl-Heinz Keim, Heimerzheim, both of Fed. Rep. of Germany

[73] Assignee: Union Rheinische Braunkohlen Kraftstoff Aktiengesellschaft, Cologne, Fed. Rep. of Germany

[21] Appl. No.: 702,662

[22] Filed: Feb. 19, 1985

[30] Foreign Application Priority Data

Feb. 23, 1984 [DE] Fed. Rep. of Germany ....... 3406536

[51] Int. Cl.$^4$ .............................................. C07C 37/00
[52] U.S. Cl. ................................... 568/804; 568/783; 568/794
[58] Field of Search ................ 568/804, 794, 716, 783

[56] References Cited

U.S. PATENT DOCUMENTS

| 4,126,750 | 11/1978 | Poe et al. | 568/804 |
| 4,329,517 | 3/1982 | Taniguchi et al. | 568/804 |
| 4,359,591 | 11/1982 | Fremery et al. | 568/804 |
| 4,400,557 | 8/1983 | Fremery et al. | 568/804 |
| 4,476,329 | 10/1984 | Chambers et al. | 568/804 |
| 4,503,269 | 3/1985 | Engel et al. | 568/804 |

FOREIGN PATENT DOCUMENTS

| 3304663 | 6/1984 | Fed. Rep. of Germany | 568/804 |
| 0101318 | 9/1978 | Japan | 568/804 |
| 0208244 | 12/1983 | Japan | 568/804 |
| 7512390 | 4/1976 | Netherlands | 568/804 |

Primary Examiner—Werren B. Lone
Attorney, Agent, or Firm—Connolly and Hutz

[57] ABSTRACT

The instant invention relates to a process for the conversion of meta/para-cresol mixtures by catalytically methylating the meta/para-cresol mixtures in their ortho-positions, separating the 2,3,6- and 2,4,6-trimethylphenols formed and converting subsequently the 2,4,6-trimethylphenol in the presence of iron oxide(s) or catalysts which contain iron oxide(s) and at least one additional oxide, to a mixture of methyl phenols, which is essentially free from meta-substituted methylphenols.

10 Claims, No Drawings

PROCESS FOR THE CONVERSION OF META/PARA-CRESOL MIXTURES

CROSS REFERENCE TO RELATED APPLICATIONS

DE-PS No. 33 04 663 (U.S. patent application Ser. No. 577,849).

BACKGROUND OF THE INVENTION

1. Field of the Invention

This invention relates to a process for the conversion of meta/para-cresol mixtures by catalytically methylating the meta/para-cresol mixtures in their ortho-positions, separating the 2,3,6- and 2,4,6-trimethylphenols formed and converting subsequently the 2,4,6-trimethylphenol in the presence of iron oxide(s) or catalysts which contain iron oxide(s) and at least one additional oxide, to a mixture of methyl phenols, which is essentially free from meta-substituted methylphenols.

2. Description of the Prior Art

The formation of 2,3,6-trimethylphenol by catalytically methylating meta-cresol is known. DE-PS No. 30 12 357 discloses for example the formation of 2,3,6-trimethylphenol in 99.5% selectivity by methylating pure m-cresol in the presence of catalysts, which contain iron oxide.

If pure para-cresol is methylated with methanol or dimethylether according to this state of the art, 2,4,6-trimethylphenol is obtained with 99% selectivity. Numerous other catalysts are known, which lead to highly selective o-substitution of phenols. For example in DE-OS No. 27 16 035 a copper-chromium-oxide catalyst is disclosed, whereas according to DE-AS No. 25 47 309, catalysts consisting of $Fe_2O_3/SiO_2/Cr_2O_3$ and $Fe_2O_3/SiO_2/Cr_2O_3/K_2O$ are well suited for the o-methylation of phenols.

2,3,6-trimethylphenol is an important starting material for the production of 2,3,6-trimethylhydroquinons, which is a component of Vitamin E.

One of the technically applied processes for the production of 2,3,6-trimethylphenol is based on open-chain units, which are condensed to a six-membered ring, which is subsequently dehydrated to form a substituted phenolring. This process is disclosed in a number of patents, among others in DE-AS No. 16 68 874 and DE-PS No. 17 93 037.

If, according to the state of the art, easily accessible mixtures of meta- and para-cresol are methylated, besides the desired 2,3,6-trimethylphenol the undesirable 2,4,6-trimethylphenol is obtained in amounts, which depend on the amount of p-cresol in the mixture.

Selective isomerizations of 2,4,6-trimethylphenol in the presence of phenol and/or phenol derivatives are disclosed in DE-PS No. 33 04 663 (U.S. patent application, Ser. No. 577,849) which has been filed by applicant. In this process a product mixture is obtained, which is essentially free of meta-substituted alkylphenols.

According to the above named U.S. patent application applicant has found that iron oxide(s) alone as well as numerous combinations of iron oxide(s) with other oxides are excellently suited for the selective isomerization and transalkylation of 2,4,6-trimethylphenol.

SUMMARY OF THE INVENTION

Object of the present invention is the production of 2,3,6-trimethylphenol starting from meta/para-cresol mixtures without the coproduction of the undesired by-product 2,4,6-trimethylphenol.

This object has been solved in a hitherto unattained manner by combining the selective ortho-methylation of meta/para-cresols with the selective isomerization and transalkylation of 2,4,6-trimethylphenol.

Thus by the instant invention a process is disclosed for the conversion of meta/para-cresol mixtures and mixtures, which contain meta/para-cresol mixtures, characterized in that the meta/para-cresol mixture is converted essentially to a mixture of 2,3,6-trimethylphenol and 2,4,6-trimethylphenol by the catalytic reaction of methanol and/or dimethylether with the meta/para-cresol mixture, that 2,3,6-trimethylphenol is separated from 2,4,6-trimethylphenol, respectively essentially separated and that the 2,4,6-trimethylphenol or a mixture, which essentially consists of 2,4,6-trimethylphenol is catalytically converted in the presence of phenol and/or alkylated phenols, to a mixture of methylphenols, which is essentially free from meta-substituted methylphenols, whereby the catalysts for the isomerization and transalkylation of 2,4,6-trimethylphenol consist of iron oxide(s) or whereby the catalysts contain iron oxide(s) and at least one oxide of at least one of the groups:

1. B, Al, Ce, Ga, In, Se, Y
2. Si, Ge, Sn, Pb, Ti, Zr, Hf
3. Cr, V, Nb, Ta, Mo, W, Re, Co, Ni, Ru, Ir
4. Li, Na, K, Rb, Cs, Be, Mg, Ca, Sr, Ba, Mn La, Cu, Zn, Cd.

DESCRIPTION OF THE PREFERRED EMBODIMENTS

In the methylating step the methylphenols and methanol and/or dimethylether are vaporized and fed into the reactor, which contains the catalyst. Usually the catalyst is applied in a fixed bed, may however also be applied in a fluid bed. Water vapor is generally added in such an amount that the molar ratio of alkylphenols to water is 1 to 1–5. The reactor is operated at a temperature of 270°–450° C., preferentially at a temperature of 330°–390° C. The reaction generally is carried out at atmospheric pressure or little pressure above the atmospheric, however it can be carried out at higher pressures up to 100 bar.

The reaction is preferentially carried out in the gas phase with residence times of 0.01–10 seconds. The molar ratio of alkylphenol to methanol and/or dimethylether is 1:0.1–10.

The isomerization-respectively transalkylation step is carried out at 200°–550° C., preferentially at 250°–450° C., pressures of 1–300 bar, with 5–180 bar preferred. The isomerization/transalkylation is preferentially carried out in the liquid phase at residence times of 0.1–10 hours, with 0.5–7 hours preferred, may however also be carried out in the gas phase. The reaction is run in an inert atmosphere, with nitrogen and/or hydrogen preferred, however other inert gases like $CO_2$, $CH_4$ or water vapor can also be used. The extensive investigations of applicant have led to the result, that iron oxide(s) alone as well as mixtures of iron oxide(s) with numerous other oxides are very well suited for the isomerization/transalkylation.

The table shows, that the inventive catalysts exhibit the particular feature that practically no meta-substituted alkylphenols are formed and that only very little residue is formed.

The inventive catalysts usually contain at least 60 weight-% iron oxide(s). With smaller iron oxide contents worse results are obtained. The catalyst can be applied in accordance with step 1 as a fluid bed, however a fixed bed is preferred.

According to the instant invention the products are 2,3,6-trimethylphenol and from 2,4,6-trimethylphenol o-cresol, p-cresol, 2,4-dimethylphenol and 2,6-dimethylphenol. Metal-alkylated phenols are of course formed in those cases, where 2,3,6-trimethylphenol has not been separated before the isomerization/transalkylation is carried out, respectively if a 2,4,6-trimethylphenol feed is charged to the isomerization/transalkylation reaction which contains meta-substituted methylphenols as by-products.

Since the products, which are obtained according to the instant invention from 2,4,6-trimethylphenol by isomerization and transalkylation are valuable products, which can be used in numerous applications, the inventive combination of reaction steps offers for the first time a hitherto unattainably economic route to the production of 2,3,6-trimethylphenol, starting from an easily accessible feedstock.

Ortho-substitution of phenols, with at least one free ortho-position by methylation in the presence of oxides as catalysts is known. The separation of 2,3,6-trimethylphenol and 2,4,6-trimethylphenol is also known. Usually a fractionated distillation is used, which can take place with or without application of vacuum. Also other separation processes like fractionated crystallization or application of molecular sieves are possible.

The application of the inventive combination of ortho-alkylation and isomerization/transalkylation satisfies a long-felt want to have available an economic route for the production of 2,3,6-trimethylphenol. It is known to the artisan, that the efforts of experts to attain this result have hitherto been futile. This is indicated by the above cited process, disclosed in DE-AS No. 16 68 874 and DE-PS No. 17 93 037, which points to a completely different direction compared to the instant invention.

The extensive investigations of applicant for many years have thus led to a result which is certainly surprising and which will presumably drastically change the present market situation for 2,3,6-trimethylphenol.

EXAMPLES AND TABLE

Examples 100 g of a technical mixture of alkylphenols, dissolved in 145 g of methanol (molar ratio 1:5) and 14 weight-% of water based on the weight of the total feed, were fed per hour to a continuously operating apparatus. The alkylphenol mixture consisted of 55 weight-% of m-cresol, 27 weight-% of p-cresol, 7 weight-% of 2,5-, 8-weight-% of 2,4- and 3 weight-% of 2,6-dimethylphenol. In a first reactor containing a o-methylation-catalyst, the ortho-methylation took place at 5 bar, a LHSV of 0,6 and a temperature of 370° C. The following catalysts were used:

(a) iron oxide, silicon dioxide, vanadium oxide, calcium oxide;
(b) iron oxide, silicon dioxide, chromium oxide, barium oxide;
(c) iron oxide, germanium oxide, chromium oxide, potassium oxide.

With each catalyst o-methylation was obtained with a selectivity of at least 99%. The portion of iron oxide was between 90-100 weight-% based on the total weight of catalyst.

The product mixtures containing 77,5 g of 2,3,6-trimethylphenol, 42,6 g of 2,4,6-trimethylphenol and 3 g of 2,6-dimethylphenol was subsequently separated by distillation. Excess methanol and water were separated by conventional means. In a first distillation column a mixture of 2,6-dimethylphenol and 2,4,6-trimethylphenol was separated over head. The remaining product was fed to a second column, where 2,4,6-trimethylphenol was distilled off in a purity of at least 99%. Small amounts of higher boiling methylated phenols were drawn off from the distillation bottom and combined with the headproduct of the first distillation column and fed to the isomerization/transalkylation reactor.

43 g of phenol were added and the reaction was carried out continuously at a temperature of 400° C., a LHSV of 0,5 and a pressure of 50-70 bar in an inert atmosphere. The same catalysts as indicated above were used.

The whole unit was operated continuously for 2000 hours without significant changes in conversion and selectivity. In addition the isomerization/transalkylation reaction has been investigated with further catalysts, as displayed in the table. The table shows that excellent results are obtained with regard to selectivity and negligible formation of residue.

The product of the isomerization/transalkylation essentially consist of approx. 20 weight-% of o-cresol, 75 weight-% of p-cresol, 15.5 weight-% of 2,4-xylenol, 7 weight-% of 2,6-xylenol, 22 weight-% of non-reacted 2,4,6-trimethylphenol, 27 weight-% of phenol and 1 weight-% of residue. The mixture can be separated in a conventional manner. According to the instant invention the feed consisting of meta/para-cresol thus can be converted in a continuously operating unit almost quantitatively into o-cresol, p-cresol, 2,4- and 2,6-xylenols and 2,3,6-trimethylphenol.

In an alternative mode of product separation, dimethylphenol was distilled off in a first column and then 2,4,6-trimethylphenol was distilled off in the subsequent column. Essentially the same results are obtained by this route, compared to the separation described above.

Excellent results are obtained with pure meta/para-cresol mixtures as a feed for example with a mixture of 60-70 weight-% of meta-cresol and 30-40 weight-% of para-cresol.

According to the instant invention the same catalysts can be used for the o-methylation step and the isomerization/transalkylation step, as well as different catalysts. The results show that meta/para-cresol mixtures, which contain additionally other methylphenols as by-products can also be converted by the inventive process with very good results.

TABLE

| Catalyst | Products in weight % | | | | | | |
|---|---|---|---|---|---|---|---|
| | Phenol | o-cresol | p-cresol | 2,4-DMP | 2,6-DMP | 2,4,6-TMP | residue |
| $Fe_3O_4$ | 28,1 | 18,9 | 5,7 | 7,7 | 5,0 | 27,7 | 4,9 |
| $Fe_2O_3/Al_2O_3$ | 23,4 | 21,0 | 7,1 | 9,7 | 6,8 | 23,7 | 7,0 |

TABLE-continued

| Catalyst | Products in weight % | | | | | | |
|---|---|---|---|---|---|---|---|
| | Phenol | o-cresol | p-cresol | 2,4-DMP | 2,6-DMP | 2,4,6-TMP | residue |
| Fe₂O₃/Cr₂O₃/SiO₂/CaO | 25,6 | 19,3 | 7,5 | 14,9 | 8,3 | 21,5 | 2,3 |
| Fe₂O₃/MoO₂/K₂O | 24,3 | 19,5 | 6,6 | 14,5 | 9,9 | 24,0 | 1,2 |
| Fe₂O₃/V₂O₅ | 25,0 | 18,1 | 6,1 | 14,1 | 8,8 | 24,1 | 3,4 |
| Fe₂O₃/SnO₂/Na₂O | 26,3 | 18,9 | 6,8 | 14,4 | 10,1 | 22,6 | 0,9 |
| Fe₂O₃/NiO GeO₂/K₂O | 24,9 | 19,3 | 6,9 | 14,4 | 10,4 | 23,5 | 0,9 |
| Fe₂O₃/Cr₂O₃ SiO₂/BaO | 25,2 | 19,1 | 7,8 | 17,0 | 8,6 | 21,4 | 0,4 |
| Fe₂O₃/RuO₂ | 25,2 | 18,8 | 6,5 | 13,7 | 8,8 | 24,2 | 2,3 |
| Fe₂O₃/MgO SiO₂/BeO | 24,5 | 20,8 | 6,0 | 15,1 | 11,1 | 22,2 | 0,8 |
| Fe₂O₃/MnO₂ K₂O | 24,9 | 19,7 | 6,1 | 14,5 | 10,6 | 22,4 | 1,8 |

DMP = dimethylphenol
TMP = trimethylphenol

What we claim is:

1. A process for the conversion of mixtures of meta- and para-cresol and solutions which comprise mixtures of meta- and para-cresol into product ortho-cresol, para-cresol, 2,4-xylenol, 2,6-xylenol and 2,3,6-trimethylphenol which comprises:
   (i) methylating meta-cresol and para-cresol in the ortho position by reacting the meta-cresol and para-cresol with methanol, dimethyl ether or a mixture thereof at a temperature of 270° to 450° C., at a pressure of atmospheric to 100 bar and in the presence of a catalyst bed without a residence time of 0.01 to 10 seconds, whereby a mixture of 2,3,6-trimethylphenol and 2,4,6-trimethylphenol is produced;
   (ii) separating a portion of the reaction mixture of step (i) containing 2,4,6-trimethylphenol from the reaction mixture and subjecting the 2,4,6-trimethylphenol-containing portion to isomerization and transalkylation at a temperature of from 200° to 550° C. and at a pressure of from atmospheric to 300 bar for 0.2 to 10 hours in the presence of a catalytic amount of iron oxide, whereby methyl phenols are produced having 1 to 3 methyl groups and being substantially free from meta-substituted methylphenols.

2. A process according to claim 1, characterized in that after methylation the dimethylphenol(s) is (are) separated and subsequently 2,4,6-trimethylphenol is separated.

3. A process according to claim 1, characterized in that the isomerization/transalkylation is carried out in an inert atmosphere.

4. A process according to claim 1, characterized in that the isomerization/transalkylation is carried out in the presence of a catalyst, which contains at least 60 weight-% of iron oxide(s).

5. A process according to claim 1, characterized in that the methylation is carried out in the gas phase and the isomerization/transalkylation in the liquid phase.

6. A process according to claim 3 wherein the inert atmosphere is nitrogen, hydrogen or methane.

7. A process according to claim 1 wherein after the methylation step (i), 2,3,6-trimethylphenol is separated from a mixture of 2,4,6-trimethylphenol and dimethylphenol and the latter mixture is fed to the isomerization-/alkylation reaction of step (ii).

8. A process according to claim 1 wherein the isomerization/transalkylation of step (ii) is catalyzed by a catalyst comprising:
   (a) at least 60% bt weight iron oxide and
   (b) up to 40% by weight of an oxide of a element selected from the group consisting of
      B, Al, Ce, Ga, In, Sc, Y,
      Si, Ge, Sn, Pb, Ti, Zr, Hf,
      Cr, V, Nb, Ta, Mo, W, Re, Co, Ni, Ru, Ir,
      Li, Na, K, Rb, Cs, Be, Mg, Ca, Sr, Ba, Mn and La.

9. A process according to claim 1 wherein the isomerization/transalkylation of 2,4,6-trimethylphenol in step (ii) is in the presence of phenol and/or methylated phenols at temperatures from 250° to 450° C., pressures of 5 to 80 bar, at reaction temperature, and residence times of 0.5 to 7 hours.

10. A process according to claim 1 wherein the methylation step (i) is carried out at 270° to 450° C. with a molar ratio of cresol to methanol and dimethylether of 1:0.1–10.

* * * * *